United States Patent
Beckmann

(10) Patent No.: US 8,800,751 B2
(45) Date of Patent: Aug. 12, 2014

(54) DISTRIBUTING DEVICE FOR SEPARATING PARTICLES IN A PARTICLE STREAM

(75) Inventor: Gert Beckmann, Haan-Gruiten (DE)

(73) Assignee: Retsch Technology, GmbH, Haan (DE)

(*) Notice: Subject to any disclaimer, the term of this patent is extended or adjusted under 35 U.S.C. 154(b) by 246 days.

(21) Appl. No.: 13/386,892

(22) PCT Filed: Jul. 20, 2010

(86) PCT No.: PCT/EP2010/004417
§ 371 (c)(1),
(2), (4) Date: Apr. 4, 2012

(87) PCT Pub. No.: WO2011/009585
PCT Pub. Date: Jan. 27, 2011

(65) Prior Publication Data
US 2012/0181149 A1   Jul. 19, 2012

(30) Foreign Application Priority Data

Jul. 24, 2009   (DE) .......................... 10 2009 034 689

(51) Int. Cl.
*G01N 15/02* (2006.01)
*B65G 11/20* (2006.01)
*G01N 35/00* (2006.01)

(52) U.S. Cl.
CPC .... *B65G 11/203* (2013.01); *G01N 2035/00574* (2013.01)
USPC ....................................... 198/560; 198/550.4

(58) Field of Classification Search
USPC ....... 198/532, 535, 550.4, 560; 193/2 B, 2 R, 193/25 R, 25 A, 31 A; 53/248, 251
See application file for complete search history.

(56) References Cited

U.S. PATENT DOCUMENTS

| | | | |
|---|---|---|---|
| 2,482,279 A * | 9/1949 | Lemmon et al. | 241/186.3 |
| 2,786,565 A | 3/1957 | Eckhart | |
| 2,945,575 A * | 7/1960 | Halbreich | 193/38 |
| 3,218,631 A | 11/1965 | Mottin | |
| 3,641,735 A * | 2/1972 | Daily et al. | 53/537 |
| 3,698,153 A * | 10/1972 | Lieberman | 53/495 |
| 3,927,508 A * | 12/1975 | Campbell, III | 53/251 |
| 4,078,698 A | 3/1978 | Bosco | |
| 4,788,812 A * | 12/1988 | Morita et al. | 53/447 |
| 5,127,212 A * | 7/1992 | Johnsen et al. | 53/540 |
| 5,143,506 A * | 9/1992 | Sticht | 414/421 |
| 5,170,610 A * | 12/1992 | Tisma | 53/447 |
| 5,309,215 A | 5/1994 | Schumann | |
| 5,911,667 A * | 6/1999 | Sanchis et al. | 53/531 |
| 6,564,528 B1 * | 5/2003 | Keegan | 53/171 |
| 6,651,801 B1 * | 11/2003 | Heckendorf | 198/406 |
| 8,015,781 B2 * | 9/2011 | Kent | 53/536 |

* cited by examiner

*Primary Examiner* — Douglas Hess
(74) *Attorney, Agent, or Firm* — Jennifer S. Stachniak; Robert W. Becker

(57) ABSTRACT

A distribution device for separating and orienting particles in a particle stream conveyed by the device to a particle-measuring device, including a conveying device with a discharge at one end for particles that are to pass in free fall to a downstream image-capturing device. At least two conducting elements are associated with the discharge and are movable relative to one another in that at least one of the conducting elements is movable under the effect of a drive mechanism. A feed gap is provided between the conducting elements for separated particles falling out of the discharge. The conducting elements are arranged in the manner of a funnel such that the feed gap is formed at an end of the funnel.

17 Claims, 1 Drawing Sheet

DISTRIBUTING DEVICE FOR SEPARATING PARTICLES IN A PARTICLE STREAM

The instant application should be granted the priority dates of Jul. 24, 2009, the filing date of the corresponding German patent application 10 2009 034 689.9, as well as Jul. 20, 2010, the filing date of the International patent application PCT/EP2010/004417.

BACKGROUND OF THE INVENTION

The invention relates to a distributing device for separating and orienting particles in a particle stream which is conducted to a particle measuring tool or device via the distributing device, wherein the distributing device comprises a conveying device with a discharge arranged at the end thereof.

A distributing device having the aforementioned features is described in DE 41 19 240 C2. To the extent that a dynamic particle measuring device is described therein, the particles, the dimensions of which are to be determined, are separated and conducted via, for example, a vibrating chute as a distributing device, and pass from the discharge disposed at its end, in free fall, between a light wave and an image-capturing device, whereby on the basis of the appropriately determined and evaluated data, the determination of the size distributions of the particles separated by the distributing device is effected.

The particles must be guided at a suitable distance past the image-capturing devices in free fall. Furthermore, in the case of elongated particles, the greatest particle dimension (the "length" of the particle) is relevant, so that an alignment of the particles prior to passing the image-capturing device is called for. Neither requirement can be fulfilled with the vibration chute as a distributing device known from DE 41 19 240 C2 without a specially configured discharge.

It is therefore an object of the present invention to embody a distributing device for the particles of a particle stream that pass a downstream image-capturing device in free fall in such a way that a directed supply of the separated particles into the region disposed between the image-capturing device and the light source is provided.

SUMMARY OF THE INVENTION

To accomplish this, the invention provides a distribution device with which associated with the discharge of the conveying device are at least two conducting elements that are moveable relative to one another and that have a feed gap provided between them for the separated particles falling out of the discharge, with the conducting elements being arranged in the manner of a funnel such that the feed gap is formed at the end of the funnel whereby at least one of the conducting elements is movable under the effect of a drive mechanism. Thus, the invention has the advantage that due to the arrangement of the conducting elements with the feed gap that is defined by them, the particles are inherently oriented as they pass the feed gap, so that the greatest particle dimensions can be reliably determined. As a consequence of the relative movement of the conducting elements relative to one another brought about by the inventively provided drive mechanism, a clogging of the feed gap, for example by particles that are disposed transversely or by the formation of bridges of particles, is avoided. The movement or movability of the conducting elements is set relative to one another in such a way that the feed gap that respectively forms due to the movement of the conducting elements ultimately to a great extent remains constant and is not significantly influenced by the relative movement of the conducting elements relative to one another.

In this connection, the inventive distribution device can have a conveying device that is provided with either a linearly circulating conveyor belt, a vibration chute or a conveying device that is otherwise caused to move, or also a simple stationary slide or other conveying plane, by means of which the particles are conveyed to the conducting elements that are disposed at the discharge.

Hereby one of the two conducting elements can respectively be movable with adjustable frequency and amplitude, whereby this movement can respectively be oriented in different directions. These directions of movement, preferably in the form of a back and forth movement, can be selected horizontally in the conveying direction of the conveying device or horizontally transverse thereto, furthermore also vertically perpendicular to the conveying plane of the conveying device. In this connection, the movement of the corresponding conducting element can selectively occur exclusively in one of the aforementioned directions of movement, or also with a direction of movement that is superimposed from the aforementioned directions of movement.

Pursuant to one embodiment of the invention, each of the two conducting elements can be movable, whereby the conducting elements can be movable at the same time, yet in different directions of movement. However, it would also be possible for the conducting elements to be movable at the same time, but respectively in the same direction of movement, whereby with the movement of the conducting elements in the same direction of movement, the movement of the conducting elements can be established in opposite directions relative to one another.

With a movement of both of the conducting elements, the movement of the conducting elements can be effected with respectively the same or however also different frequencies, and also with the same amplitude or with different amplitudes.

In a first arrangement of the conducting elements, the conducting elements can be oriented transverse to the discharge direction of the conveying device, whereby the conducting element that in the direction of conveying of the conveying device is spaced from the discharge of the conveying device acts as an impingement or deflection element. With such an orientation of the conducting elements relative to the conveying device, one of the conducting elements, or both of the conducting elements, can respectively move in the directions of movement as described above.

With such an orientation of the conducting elements, the effectiveness of the distribution device can be improved in that an additional discharge element adjoins the discharge of the conveying device, such additional discharge element extending into the feed gap formed by the conducting elements, whereby the discharge element can be comprised of an essentially planar plate that adjoins the discharge of the conveying device in a vertical orientation.

Pursuant to one embodiment of the invention, the discharge element can be movable under the effect of a drive mechanism. It is to be understood that to this extent the discharge element can correspondingly have the same directions of movement as was described in conjunction with the conducting elements, namely horizontally in the direction of conveyance of the conveying device, transverse thereto, as well as also vertically perpendicular to the conveying plane of the conveying device. With a discharge element that is to such an extent movably arranged, it does not matter whether the rear conducting element, which is disposed across from the front element that serves as an impingement or deflection element, and hence is disposed behind or below the discharge in the direction of discharge, is not movable or however is itself movably arranged.

In an alternative arrangement of the conducting elements, the conducting elements, which are disposed opposite one another, can extend in the direction of conveyance of the conveying device, consequently in the longitudinal direction thereof. Hereby, the particles are delivered in the longitudinal direction between the conducting elements, whereby in this case the discharge is positioned between the conducting elements, which are arranged in the manner of a funnel. Also with such a positioning of the conducting elements, one of the conducting elements, or both of the conducting elements, can respectively move in the indicated directions of movement.

Pursuant to one embodiment of the invention, the conducting elements and/or the discharge element can have a plate-like configuration.

The function of the conducting elements can be improved if pursuant to one embodiment of the invention the conducting elements and/or the discharge element is made of an elastic material, insofar as the conducting elements can then yield to the impact of the particles. Due to the elasticity of the conducting elements, and/or of the discharge element, their effect or action brought about by the introduced movement can also be reinforced.

With respect to the construction of the conducting elements and/or the discharge element, the respective elements can be comprised of individual segments that are movable relative to one another, so that the conducting elements and/or the discharge element are partially, or independently, movable.

In this connection, pursuant to various embodiments of the invention, the segments of conducting elements and/or discharge element can be displaceable relative to one another, for example parallel to one another, or can also be disposed so as to be pivotable relative to one another. The segments can also be individually suspended on swivel joints, and hence are respectively pivotable.

With regard to the drive mechanisms for carrying out the movement of the conducting elements and/or the discharge element, the drive mechanisms can be configured as rotary drives, with or without gear mechanisms on the output side, or as linear drives, with or without gear mechanisms on the output side. Such drive mechanisms can selectively include electrical, hydraulic or pneumatic drive mechanisms.

BRIEF DESCRIPTION OF THE DRAWINGS

Exemplary embodiments of the invention, which will be described subsequently, are illustrated in the drawing, in which.

DESCRIPTION OF SPECIFIC EMBODIMENTS

Figure 1:
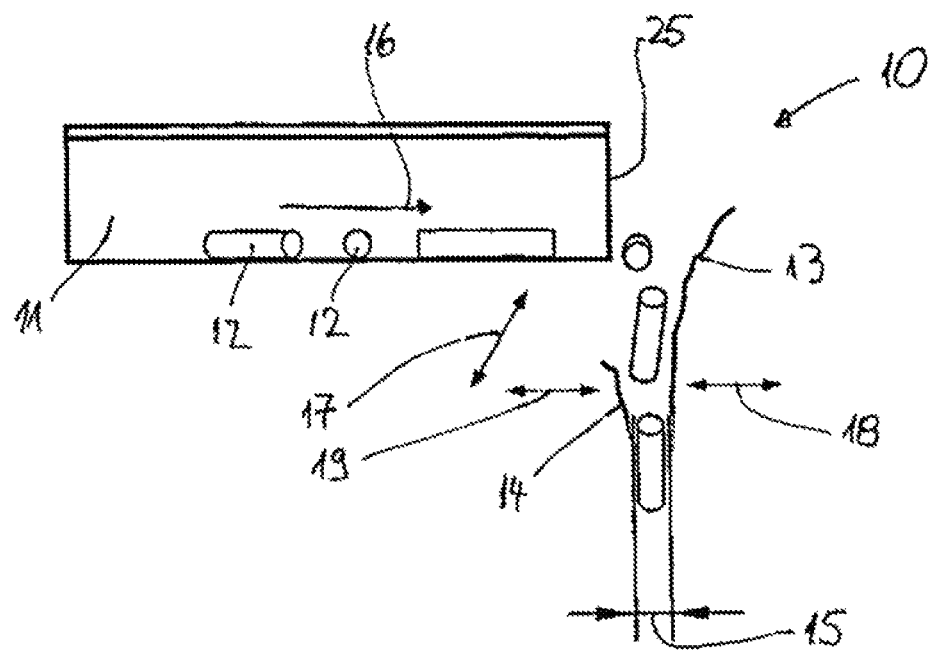
FIG. 1 is a schematic illustration showing a distributing device having two conducting elements.

The distributing or distribution device 10, which is schematically illustrated in FIG. 1, is comprised of a conveying device 11 on which are disposed particles 12 that, by means of a movement of the conveying device 11, are transported to a discharge 25 that is disposed at the end of the conveying device; the particles fall off of the conveying device 11 at the discharge 25. In this connection, the conveying device 11 is cause to move in such a way that there results a direction of conveyance for the particles 12 to the discharge 25, with the direction of conveyance being indicated by the arrow 16, whereby the conveying device 11, via an associated, not further illustrated, drive, has imparted thereto a movement having superimposed directions of movement that include a back and forth movement of the conveying device 11 in the elements relative to the conveying device, one of the conducting elements, or both of the conducting elements, can respectively move in the direction of movement as described above.

The distributing or distribution device 10, which is schematically illustrated in FIG. 1, is comprised of a conveying device 11 on which are disposed particles 12 that, by means of a movement of the conveying device 11, are transported to a discharge 25 that is disposed at the end of the conveying device; the particles fall off of the conveying device 11 at the discharge 25. In this connection, the conveying device 11 is cause to move in such a way that there results a direction of conveyance for the particles 12 to the discharge 25, with the direction of conveyance being indicated by the arrow 16, whereby the conveying device 11, via an associated, not further illustrated, drive, has imparted thereto a movement having superimposed directions of movement that include a back and forth movement of the conveying device 11 in the direction of conveyance 16, as well as a vertical movement of the conveying device 11 in a plane that is perpendicular to the conveying plane. This movement of the conveying device 11 is indicated by the arrow 17.

In the illustrated embodiment, associated with the discharge 25 of the conveying device 11 are two conducting elements 13 and 14, which are disposed transverse to the direction of conveyance (arrow 16) and that comprise a forward conducting element 13, which in the direction of conveyance pursuant to the arrow 16 is spaced from the discharge 25 and to this extent acts as an impingement or deflection element, and a rear conducting element 14 that is disposed across from the front conducting element 13 and faces the discharge 25 of the conveying device 11. In this connection, the conducting elements 13 and 14 are arranged in such a way that they form a funnel that is open toward the discharge 25, and at their lower end form a defined feed gap 15 by means of which the particles 12 leave the distributing device 10 in order to subsequently pass in free fall to the downstream image-capturing device. The two conducting elements 13, 14 are preferably embodied as plate-type elements, and are comprised of an elastic or resilient material. Although not further illustrated, the plate-type elements can have a segmented configuration, whereby the individual segments can be displaceable relative to one another, can be pivotable, or can be individually suspended on swivel joints.

In the embodiment illustrated in FIG. 1, the front conducting element 13, as well as the rear conducting element 14, have a movement imparted to them by means of an associated drive mechanism, whereby in the illustrated embodiment the movement of the two conducting elements 13 and 14 takes place in the direction of conveyance 16 of the conveying device 11 to the extent that the conducting elements 13 and 14 therefore carry out a corresponding back and forth movement toward or away from the discharge 25 respectively, as indicated by the movement arrows 18 and 19. To the extent that the two conducting elements 13 and 14 carry out a parallel movement, it should preferably be provided that the movement of the conducting elements 13 and 14 are oppositely directed relative to one another; in other words, if the rear conducting element 14 moves toward the discharge 25 during its back and forth movement, the front conducting element 13 at the same time moves away from the discharge 25.

To realize the invention it is, however, for example also sufficient if only one of the two conducting elements, in particular the front conducting element 13, moves, with the other conducting element being stationary. For the movement of the conducting elements 13 and 14, it is also possible to provide directions of movement other than those illustrated, for example a movement of the conducting elements horizontally transverse to the direction of conveyance 16 of the conveying device 11, or vertically perpendicular to the conveying plane of the conveying device 11. Superimposed directions of movement can also be established for the conducting elements 13 and 14 similar to the movement of the conveying device 11 pursuant to the arrow 17. In this connection, the movement of the conducting elements can occur with the same frequency and/or amplitude as well as with respectively different frequencies and/or amplitudes.

Figure 2:
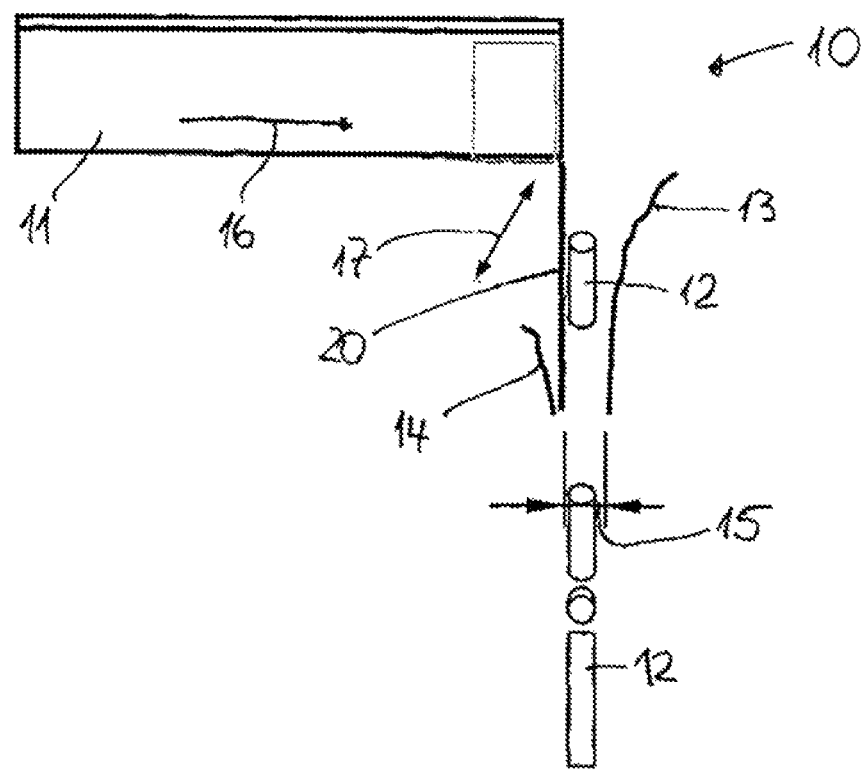
FIG. 2 shows the subject matter of FIG. 1 with the additional arrangement of a discharge element.

The embodiment illustrated in FIG. 2 differs from the embodiment illustrated in FIG. 1 in that adjoining the discharge 25 of the conveying device 11 is an additional dump or discharge element 20, which is embodied in the form of a vertically oriented plate that extends into the feed gap 15 formed by the conducting elements 13 and 14. In the illustrated embodiment, the front conducting element 13 carries out a back and forth movement in conformity with the direction of conveyance 16 of the conveying device 11, as indicated by the arrow 18 in FIG. 1; the rear conducting element 14 is stationary, to the extent that it is covered by the discharge element 20. The discharge element 20 is, in turn, again movable, and in particular in the illustrated embodiment with superimposed directions of movement in the same form as described for the conveying device 11 as indicated by the arrow 17. To this extent, with such a configuration, it is also possible, in order to accomplish its movement, to couple the discharge element 20 with the drive for the conveying device 11, so that the movements of the conveying device 11 and the discharge element 20 are in the same direction. Of course, it would also be possible to provide the discharge element 20 with its own drive, by means of which an independent movement can be imparted to the discharge element 20, in a manner similar to what was described for the front conducting element 13 or the rear conducting element 14.

The features of the subject matter of these documents disclosed in the preceding description, the patent claims, the abstract and the drawing can be important individually as well as in any desired combination with one another for realizing the various embodiments of the invention.

The specification incorporates by reference the disclosure of German 10 2009 034 689.9 filed Jul. 24, 2009, as well as International application PCT/EP2010/004417 filed Jul. 20, 2010.

The present invention is, of course, in no way restricted to the specific disclosure of the specification and drawings, but also encompasses any modifications within the scope of the appended claims.

The invention claimed is:

1. A distribution device for a separation and orientation of particles in a particle stream that is conveyed by said distribution device to a particle-measuring device, comprising:
a conveying device having disposed at one end thereof a discharge for particles that are to pass in free fall to a downstream image-capturing device; and
at least two conducting elements associated with said discharge of said conveying device, wherein said conducting elements are movable relative to one another in that at least one of said conducting elements is configured to be movable under the effect of a drive mechanism, further wherein a feed gap is provided between said conducting elements for separated particles falling out of said discharge, and wherein said conducting elements are arranged in the manner of a funnel such that said feed gap is formed at an end of said funnel, wherein the particles are inherently oriented as they pass the feed gap, wherein the feed gap that respectively forms due to the movement of the conducting elements remains constant and is not significantly influenced by the relative movement of the conducting elements relative to one another, so that the greatest particle dimensions can be reliably determined.

2. A distribution device according to claim 1, wherein one of said at least two conducting elements is movable horizontally in a direction of conveyance of said conveying device, or horizontally transverse to the direction of conveyance of said conveying device, or vertically perpendicular to a conveying plane of said conveying device, and with adjustable frequency and amplitude.

3. A distribution device according to claim 1, wherein said at least two conducting elements are disposed across from one another to form said funnel, and wherein said conducting elements are simultaneously movable in different directions of movement.

4. A distribution device according to claim 1, wherein said at least two conducting elements are disposed across from one another to form said funnel, and wherein said conducting elements are simultaneously movable in the same or parallel direction of movement.

5. A distribution device according to claim 4, wherein said conducting elements are simultaneously movable in a parallel direction, and wherein the movement of said conducting elements is established in opposite directions relative to one another.

6. A distribution device according to claim 1, wherein movement of said conducting elements is respectively effected with the same frequency or with different frequencies.

7. A distribution device according to claim 1, wherein movement of said conducting elements is effected with the same amplitude or with different amplitudes.

8. A distribution device according to claim 1, wherein said conducting elements are oriented transverse to a direction of discharge of said conveying device, and wherein that conducting element that in a direction of conveyance of said conveying device is spaced from said discharge of said conveying device, acts as an impingement or deflection element.

9. A distribution device according to claim 1, which further includes an additional discharge element that adjoins said discharge of said conveying device, wherein said additional discharge element extends into said feed gap that is formed by said conducting elements.

10. A distribution device according to claim 9, wherein said additional discharge element is configured to be movable under the effect of a drive mechanism.

11. A distribution device according to claim 1, wherein said at least two conducting elements are disposed across from one another, and wherein said conducting elements extend in a direction of conveyance of said conveying device.

12. A distribution device according to claim 11, wherein said discharge of said conveying device is positioned between said conducting elements that are arranged in the manner of a funnel.

13. A distribution device according to claim 1, wherein said conducting elements, and/or an additional discharge element that adjoins said discharge of said conveying device, have a plate-shaped configuration.

14. A distribution device according to claim 13, wherein said conducting elements and/or said additional discharge element are comprised of individual segments that are configured to be movable relative to one another, displaceable relative to one another, pivotable, or respectively rotatable.

15. A distribution device according to claim 1, wherein said conducting elements, and/or an additional discharge element that adjoins said discharge of said conveying device, are made of an elastic material.

16. A distribution device according to claim 1, wherein drive mechanisms for carrying out movement of said conducting elements, and/or of an additional discharge element that adjoins said discharge of said conveying device, are rotary drives or linear drives, with or without a gear mechanism on an output side.

17. A distribution device according to claim 16, wherein said drive mechanisms are configured as electrical, hydraulic or pneumatic drive mechanisms.

* * * * *